(12) United States Patent
Norris et al.

(10) Patent No.: US 11,801,394 B1
(45) Date of Patent: Oct. 31, 2023

(54) SYSTEMS AND METHODS FOR COVERTLY CREATING ADVERSE HEALTH EFFECTS IN SUBJECTS

(71) Applicants: Elwood Norris, Poway, CA (US); Seth Putterman, Los Angeles, CA (US)

(72) Inventors: Elwood Norris, Poway, CA (US); Seth Putterman, Los Angeles, CA (US)

( * ) Notice: Subject to any disclaimer, the term of this patent is extended or adjusted under 35 U.S.C. 154(b) by 0 days.

(21) Appl. No.: 18/152,349

(22) Filed: Jan. 10, 2023

(51) Int. Cl.
*A61N 2/02* (2006.01)
*A61N 2/00* (2006.01)
*F41H 13/00* (2006.01)

(52) U.S. Cl.
CPC ............ *A61N 2/02* (2013.01); *A61N 2/006* (2013.01); *F41H 13/0043* (2013.01); *F41H 13/0081* (2013.01)

(58) Field of Classification Search
CPC ............ F41H 13/0043; F41H 13/0081; F41H 13/0068; F41H 13/0075
See application file for complete search history.

(56) References Cited

U.S. PATENT DOCUMENTS

| | | | |
|---|---|---|---|
| 2,922,999 A | 1/1960 | Carlin | |
| 3,557,899 A * | 1/1971 | Longinette | F41H 13/0081 601/2 |
| 3,566,347 A | 2/1971 | Flanders | |
| 3,612,211 A * | 10/1971 | Clark, III | F41H 13/0081 367/92 |
| 3,951,134 A | 4/1976 | Malech | |
| 4,349,898 A | 9/1982 | Drewes et al. | |
| 4,858,612 A | 8/1989 | Stocklin | |
| 4,884,809 A | 12/1989 | Rowan | |
| 6,359,835 B1 | 3/2002 | Gayl | |
| 7,841,989 B2 | 11/2010 | Kiefer et al. | |
| 7,994,962 B1 * | 8/2011 | Ben-Shmuel | H01Q 19/18 342/13 |
| 8,049,173 B1 * | 11/2011 | Brown | H01Q 19/00 250/341.7 |
| 8,661,961 B2 | 3/2014 | Rosenberg et al. | |
| 9,470,214 B2 | 10/2016 | Kennedy | |
| 9,500,447 B1 * | 11/2016 | Cannon, Jr. | F41H 13/0043 |
| 9,872,100 B2 | 1/2018 | Henry et al. | |
| 10,506,936 B2 | 12/2019 | Clark et al. | |

(Continued)

OTHER PUBLICATIONS

Bozovic and Hudspeth, Hair-bundle Movements Elicited by Transepithelial Electrical Stimulation of Hair Cells in the Sacculus of the Bullfrog, Feb. 4, 2023, 6 pages, vol. 100, PNAS, New York.

(Continued)

*Primary Examiner* — Joshua E Freeman
(74) *Attorney, Agent, or Firm* — Jason R. Jones

(57) ABSTRACT

A method for covertly creating adverse health effects in a human subject includes generating at least one electromagnetic wave at a frequency within the range of about 300 MHz (megahertz) and about 300 GHz (gigahertz). The at least one electromagnetic energy wave is pulsed at a pulse frequency within a target range of human neural oscillations. At least one ultrasonic audio wave is generated at a frequency greater than about 20 kHz (kilohertz). The at least one audio wave is pulsed at the pulse frequency. Each of the at least one pulsed electromagnetic wave and the at least one ultrasonic audio wave are remotely transmitted to the subject's brain.

15 Claims, 5 Drawing Sheets

(56) References Cited

U.S. PATENT DOCUMENTS

| | | | |
|---|---|---|---|
| 2005/0226438 A1 | 10/2005 | Norris et al. | |
| 2006/0256559 A1 | 11/2006 | Bitar | |
| 2011/0316678 A1* | 12/2011 | Duge | F41H 13/00 340/407.1 |
| 2012/0002193 A1* | 1/2012 | Elliott | G01K 17/003 356/121 |
| 2012/0212368 A1* | 8/2012 | Todd | F41H 13/0068 342/350 |
| 2016/0377391 A1* | 12/2016 | Rubtsov | F21L 4/027 315/297 |
| 2018/0252506 A1* | 9/2018 | Hoboy | F41H 13/0087 |
| 2020/0108925 A1* | 4/2020 | Smith | B64C 39/024 |
| 2023/0099600 A1* | 3/2023 | Blate | F41H 13/005 250/493.1 |

OTHER PUBLICATIONS

Fomenko et al., Systematic Examination of Low-intensity Ultrasound Parameters on Human Motor Cortex Excitability and Behavior, elife, Nov. 25, 2020, 30 pages.

Frey AH, Auditory System Response to Radio Frequency Energy, Dec. 1961, 3 pages, Aerospace Med.

Kubanek et al., Remote, Brain Region-Specific Control of Choice Behavior with Ultrasonic Waves, Science Advances, May 20, 2020, 9 pages, vol. 6.

Lubner et al., Review of Audio vestibular Symptoms Following Exposure to Acostic and Electromagnetic Energy Outside Conventional Human Hearing, Frontiers in Neurology, Apr. 28, 2020, 12 pages, vol. 11.

Romanenko et al., The Interaction Between Electromagnetic Fields at Megahertz, Gigahertz and Terahertz Frequencies with Cells Tissues and Organisms: Risk and Potential, Interface, Nov. 14, 2017, 22 pages, vol. 14, rsif.royalsocietypublishing.org.

* cited by examiner

US 11,801,394 B1

SYSTEMS AND METHODS FOR COVERTLY CREATING ADVERSE HEALTH EFFECTS IN SUBJECTS

BACKGROUND OF THE INVENTION

Field of the Invention

The present technology relates generally to less-than lethal approaches to behavior modification of targeted subjects. More particularly, the present technology relates to such techniques that can be accomplished without the subject becoming aware of the presence of any outside influence.

Related Art

Numerous less-than-lethal conventional systems have been developed to influence or control the behavior of target subjects without requiring physical contact with the subject. Examples include directing high intensity sounds toward the subjects, exposing the subjects to strobe lights at particular frequencies, directing highly directional ultrasonic waves toward the subjects, and the like. While each of these systems have performed with some success, they generally suffer from the fact that the subject becomes quickly aware that some outside influence is causing him or her distress. For example, the use of audible sound or light provides immediately alerts the subject of an issue. The subject can take evasive action by simply blocking or protecting his or her hearing or vision.

SUMMARY OF THE INVENTION

In accordance with one aspect of the technology, a method is provided for covertly creating adverse health effects in a human subject. The method can include generating at least one electromagnetic wave at a frequency within the range of about 300 MHz (megahertz) and about 300 GHz (gigahertz). The at least one electromagnetic energy wave can be pulsed at a pulse frequency within a target range of human neural oscillations. The at least one pulsed electromagnetic wave can be remotely transmitted to the subject's brain.

In accordance with another aspect of the technology, a method for covertly creating adverse health effects in a human subject is provided, including generating at least one ultrasonic audio wave at a frequency greater than about 20 kHz (kilohertz) and pulsing the at least one ultrasonic audio wave at a pulse frequency within a target range of human neural oscillations. The at least one pulsed ultrasonic audio wave can be remotely transmitted to the subject's brain.

In accordance with another aspect of the present technology, a method for covertly creating adverse health effects in a human subject is provided, including generating at least one electromagnetic wave at a frequency within the range of about 300 MHz (megahertz) and about 300 GHz (gigahertz) and pulsing the at least one electromagnetic energy wave at a pulse frequency within a target range of human neural oscillations. At least one ultrasonic audio wave can be generated at a frequency greater than about 20 kHz (kilohertz). The at least one ultrasonic audio wave can be pulsed at the pulse frequency. Each of the at least one pulsed electromagnetic wave and the at least one ultrasonic audio wave can be transmitted to the subject's brain.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

The following drawings illustrate exemplary embodiments for carrying out the invention. Like reference numerals refer to like parts in different views or embodiments of the present invention in the drawings.

DETAILED DESCRIPTION

Figure 1:
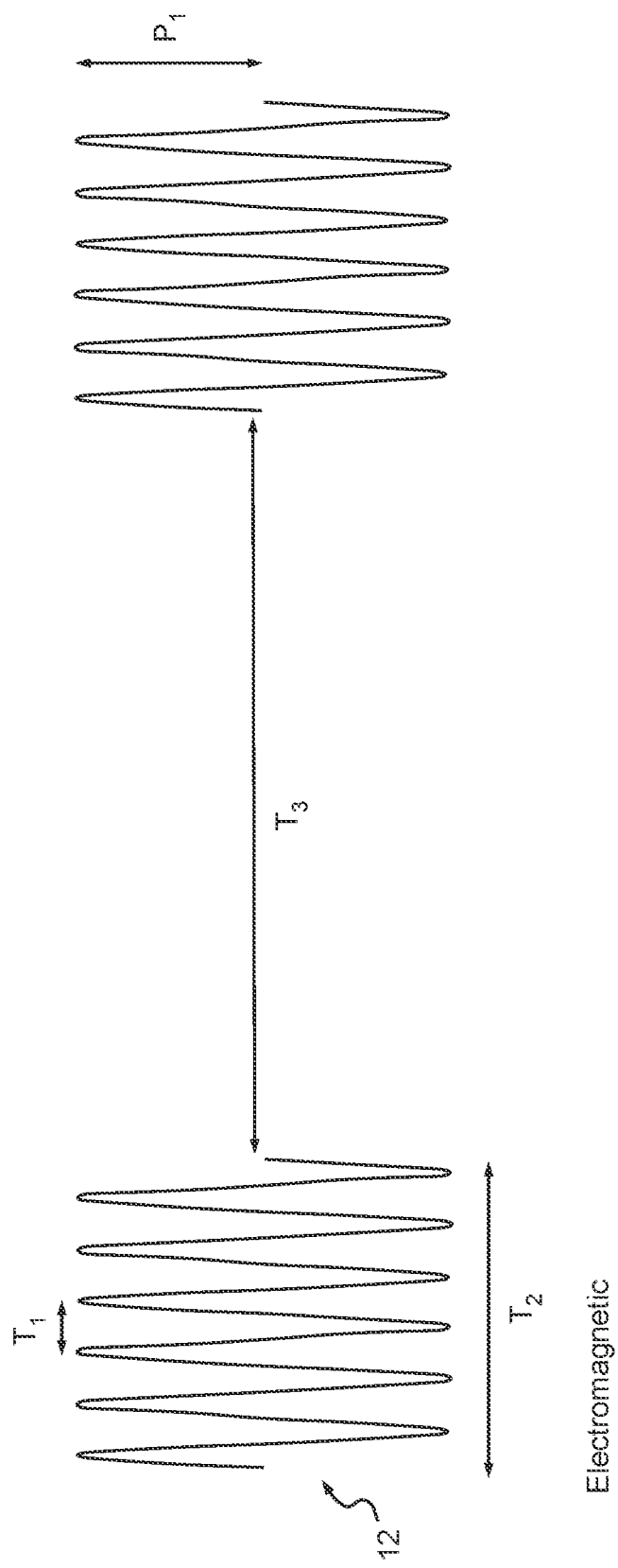
FIG. 1 is a graph showing an exemplary electromagnetic waveform generated in accordance with an embodiment of the technology.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

Definitions

As used herein, the singular forms "a" and "the" can include plural referents unless the context clearly dictates otherwise. Thus, for example, reference to an "electromagnetic wave" can include one or more of such waves.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Invention

The present technology relates generally to systems and methods for covertly creating adverse health effects in animal subjects. While the present technology can be used successfully with a variety of animals, it can be particularly well adapted for influencing human behavior. As such, the following discussion will focus on the use of the technology with humans, with the understanding that the technology is in no way limited to this.

Advantageously, the present technology can be implemented without the intended subject becoming aware of the causes of the adverse health effects. The present technology can be directed toward the subject remotely, and can be implemented from behind walls, windows, etc. Thus, during the treatment of the subject, he or she has no knowledge than an outside actor is attempting to influence his or her well-being. Once the subject is no longer exposed to the current technology, there is little to no evidence that any outside influence acted upon the subject, even though the effects of the exposure may still be perceived by the subject. Thus, the subject remains completely unaware that any attempt has been made to influence his or her behavior, even though he or she may still be experiencing the adverse health effects.

The present inventors are aware of previous work performed by Charles Bovill that has become known as a the "bucha" or "flicker" effect. Bovill taught that directing a strobe light emitting pulses in the range of 10-30 Hz (hertz) can produce an adverse effect in a percentage of the population—the subject will experience giddiness, nausea, vertigo, etc. In addition, Allan Frey discovered that directing microwaves on the order of 1.3 GHz (gigahertz) toward the head of a subject can cause a subject to experience the sensation of sound. While each of these methods, and others like them, may be used with some success to the modify the behavior of animal subjects, they suffer from the disadvantage that the subject is aware of some adverse event—he or she can see the lights, or hear the audio (developed traditionally or through the Frey effect), and is thus aware that he or she can take some action to avoid the effect.

The present technology addresses these shortcomings in the prior art by covertly creating adverse health effects in subjects in a manner by which the subject does not consider that an outside influence is acting upon them. He or she simply feels ill and acts accordingly. The present inventors believe that the technology can be utilized to covertly create symptoms in subjects including nausea, cognitive difficulties, vertigo, etc. Once the subject experiences such symptoms, he or she is either unable or unwilling to continue the activity in which they are engaged. This can be achieved without providing the subject any clue that an outside actor is responsible for the symptoms.

Broadly speaking, the present technology directs electromagnetic or ultrasonic waveforms toward a subject's head. The waveforms are pulsed at frequencies that correspond to a target range of human neural oscillations. Such neural oscillations are naturally occurring in animals, particularly humans, and are believed to originate from the electrical activity of human brain. The best known examples of these are alpha and beta waves (or alpha and beta rhythms). Alpha rhythms are understood to be neural oscillations in the frequency range of 8-12 Hz, likely originating from the synchronous and coherent (in phase or constructive) electrical activity of thalamic pacemaker cells in humans. Beta rhythms are understood to be a neural oscillation (brainwave) in the brain with a frequency range of between 12.5 and 30 Hz (12.5 to 30 cycles per second). Beta waves can be split into three sections: low beta waves (12.5-16 Hz), beta waves (16.5-20 Hz) and high beta waves (20.5-28 Hz).

The present inventors believe that directing electromagnetic energy waves and/or hypersonic waves pulsed at frequencies corresponding to the naturally-occurring alpha or beta rhythms of a subject can result in the subject experiencing adverse health effects similar to those produced by the bucha effect utilizing light. The energy waves directed toward the subject can be selected from a range of frequencies. Visible light, typically in the range of 400 to 800 THz (terahertz), was pulsed or strobed within the Alpha or Beta range by Bovill to create the bucha, or flicker, effect. The present inventors believe, however that electromagnetic waves of sufficient intensity at a wide range of frequencies can produce the same result. For example, electromagnet waves at frequencies far below and above the visible light spectrum. The present technology does so, however, with wavelengths typically undetectable by humans. In this manner, the subjects in whom the effect is created remain unaware that they have been targeted.

In one aspect of the technology, a method is provided for covertly creating adverse health effects in a human subject. The method can include generating at least one electromagnetic wave at a frequency within the range of about 300 MHz (megahertz) and about 300 GHz (gigahertz). The electromagnetic wave can be pulsed at a pulse frequency within a target range of human neural oscillations. The resulting waveform can be remotely transmitted to a subject's brain, resulting in the subject experience negative or adverse health effects.

FIG. 1 illustrates one specific example in accordance with an embodiment of the technology. As shown, an electromagnetic waveform 12 can be generated with a period of $T_1$, in this example $T_1$ is about 1 ns (nanosecond). This results in a frequency of about 1 GHz (gigahertz)—within the range generally referred to as microwaves. The waveform can be generated for time interval $T_2$, in this case about 100 us (microsecond). The waveform can be pulsed at time intervals $T_3$ of about 100 ms (millisecond), which results in a discrete waveform being generated at a frequency of about 10 Hz. In this example the pulse frequency is 10 Hz, within the alpha wave range of 8-12 Hz. This pulse frequency, however, can be chosen as any discrete frequency within this range of about 8 Hz to about 12 Hz.

It is believed that the specific pulse frequency required for any particular individual will vary. Some individuals may feel adverse effects at 8.5 Hz, for example, while others may not respond unless the pulse frequency is about 11 Hz. For this reason, the pulse frequency generated can correspond to one of a plurality of discrete frequencies, and can be varied until the subject responds accordingly. Once the appropriate pulse frequency is discovered, the pulse frequency need not be adjusted for that particular subject. In another example, the pulse frequency can be continuously varied within the target range of frequencies, so as to sweep through the target range of frequencies. It is believed that this sweep will capture the necessary pulse frequency sufficiently often to generate the desired effect by the subject. While the sweep rate can vary, in one example the pulse frequency can sweep through the range every one to five seconds.

The power level $P_1$ of the example of FIG. 1 can be varied to achieve the desired result without causing any permanent anatomical damage. In this example, the power level can average about 0.3 mW/cm$^2$ (milliwatts per centimeter squared), with peak power of about 0.3 W/cm$^2$. The frequency of the electromagnetic waveform can be selected from a range of frequencies. In one embodiment, a typical microwave oven magnetron can be utilized, operating at around 2.5 GHz.

In addition to generating a pulse frequency within the subject's alpha rhythm range, the pulse frequency can be selected to correspond with the subject's beta rhythm range, that is between about 12.5 Hz to about 30 Hz. In other examples, sub-beta ranges can be targeted, including without limitation, a range of about 12.5 Hz to about 16 Hz; a range of about 16.5 Hz to about 20 Hz, and a range of about 20.5 Hz to about 28 Hz.

Figure 2:
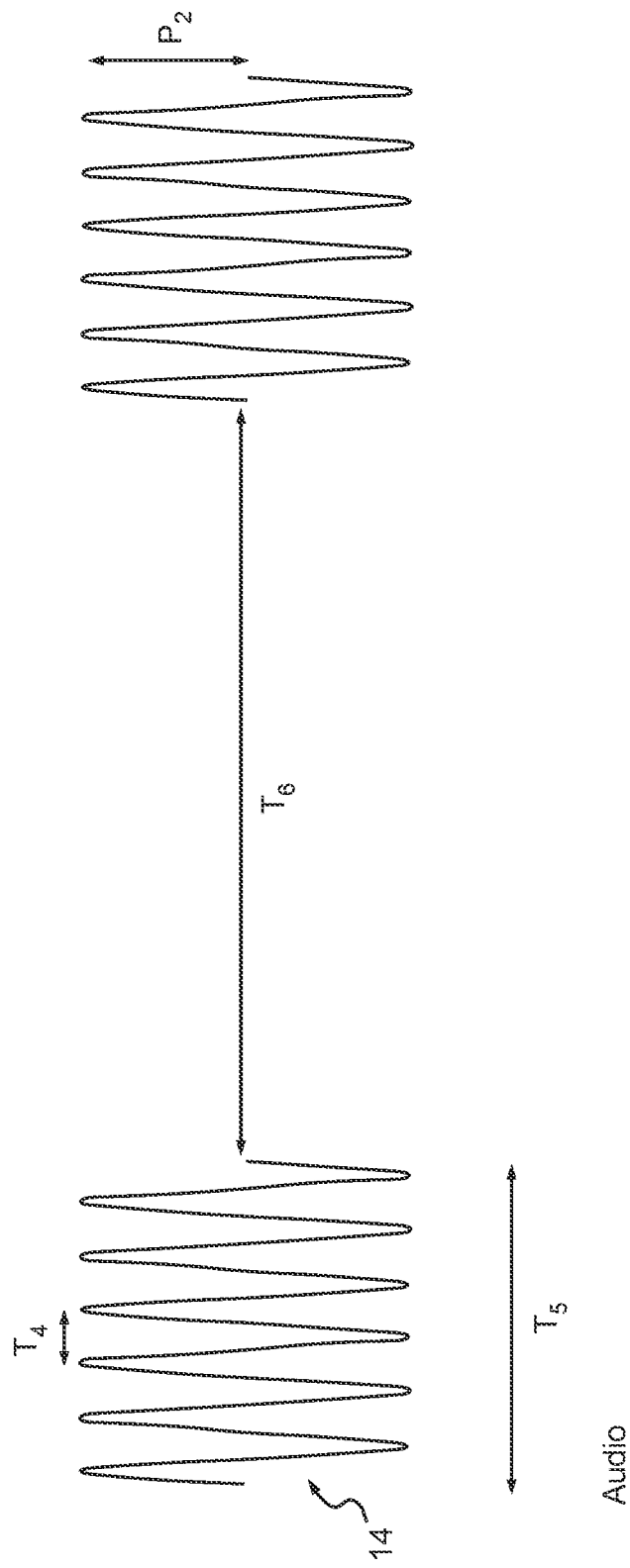
FIG. 2 is a graph showing an exemplary ultrasonic audio waveform generated in accordance with an embodiment of the technology.

FIG. 2 illustrates a further exemplary implementation of the technology in which an ultrasonic waveform 14 can be generated. In this example, $T_4$ is about 40 vs, $T_5$ is about 50 ms, $T_6$ is about 100 ms, and the acoustic field $P_2$ at the target is between about 120 dB (decibel) and about 140 dB. In one example, the acoustic field $P_2$ at the target is about 130 dB. These values are generally evaluated at the location of the subject: they may be greater at the source. In some embodiments, the acoustic field may be as high as 130-160 dB at the source, to achieve a field of 120-140 dB at the subject. In this example, the pulse frequency is again about 10 Hz. In this example, while an audio waveform is utilized, the frequency is selected in the ultrasonic range (e.g., greater than about 20 kHz) to ensure that the subject cannot hear the waveform, and thus is not alerted to the presence of an outside actor.

The carrier frequency utilized in generating the ultrasonic waveform can be selected to balance various design goals. While a carrier frequency of about 40 kHz can be utilized, this can result in generating audible subharmonic waves (e.g., ⅓ of 40 kHz, or about 13 kHz, which can be detected by some humans). If a carrier frequency of about 42-45 kHz is used instead, the subharmonic waves generated may be less likely to be heard by the subject (e.g., 14 to 15 kHz, which are closer to being outside the audible range for all humans). The present inventors have found, however, that raising the carrier frequency too high can result in significant loss of range. Thus, the carrier frequency used is generally not higher than about 50 kHz.

Figure 3:
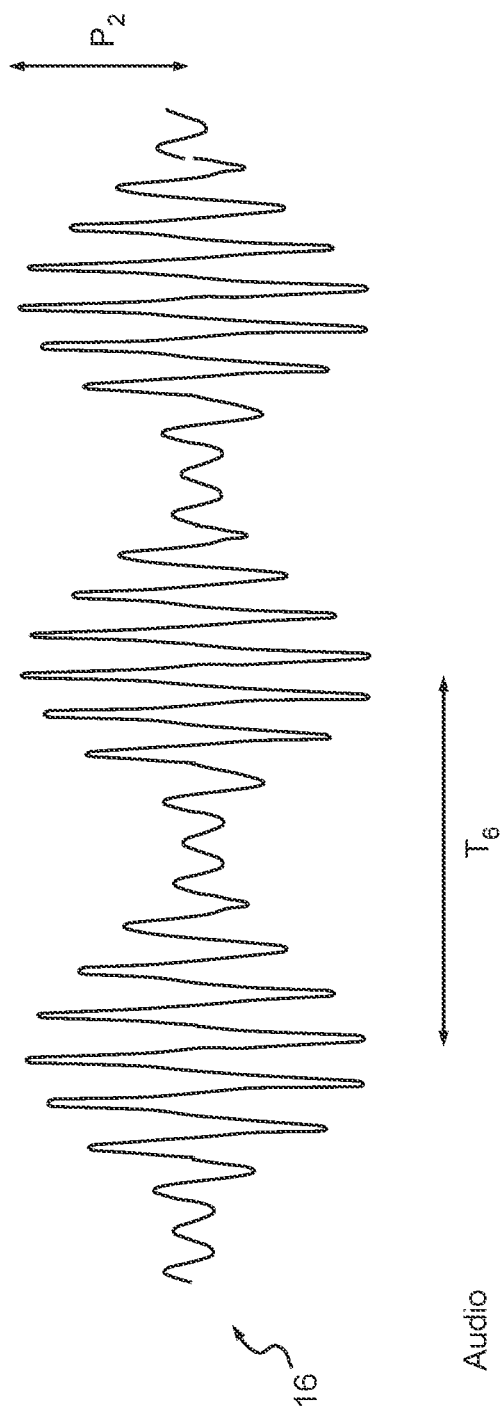
FIG. 3 is a graph showing an exemplary modulated ultrasonic audio waveform generated in accordance with an embodiment of the technology.

FIG. 3 illustrates an exemplary modulated ultrasonic waveform 16 that can be generated through a variety of methods known in the art. The peak-to-peak pulse frequency is again shown here by example as about 10 Hz.

Figure 4:
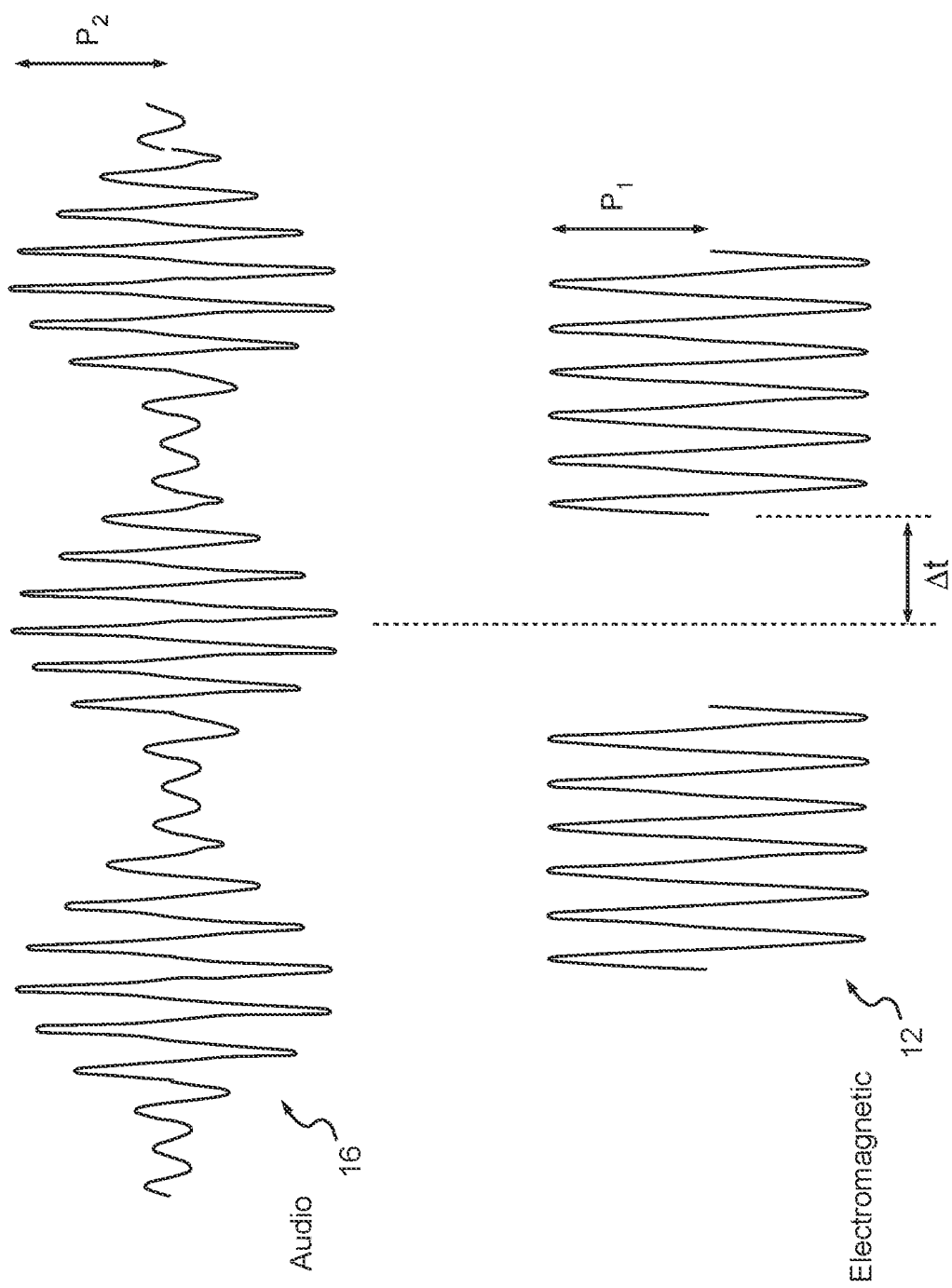
FIG. 4 is a graph showing an exemplary set of waveforms including an electromagnetic waveform and an ultrasonic audio waveform generated simultaneously in accordance with an embodiment of the technology.

FIG. 4 illustrates an embodiment in which a pair of waveforms 12, 16 are generated and directed toward the subject's head. In this example, both an electromagnetic wave 12 and modulated ultrasonic wave 14 are directed toward the subject. The inventors believe that the two waveform types can synergistically excite the subject's brainwaves to create the desired effect.

In this example, while the pulsed frequency of each wave is shown as being similar, one of the waveforms can be phased relative to the other waveform by a delay of Δt from between about 10 ms to about 50 ms. The present inventors believe phasing the waveforms can compensate for the difference in response time of the human brain to audio and electromagnetic waveforms.

Figure 5:
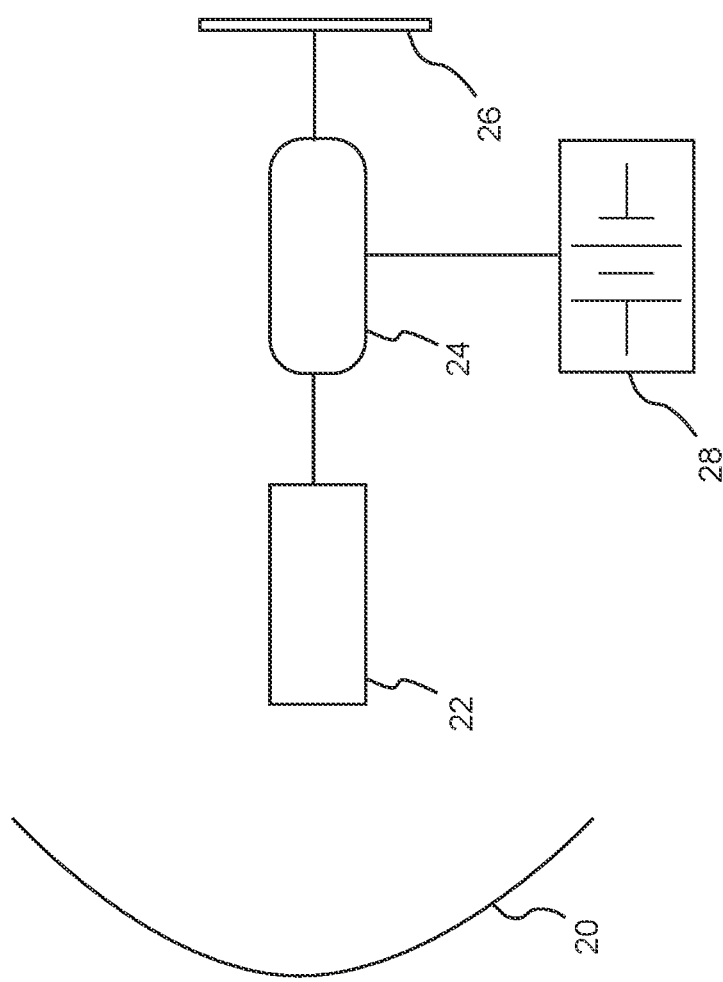
FIG. 5 is an exemplary waveform generating device in accordance with an embodiment of the technology.

FIG. 5 illustrates an exemplary assembly that can be used to generate the waveforms discussed above. In this example, a parabolic microwave antenna 20 can reflect microwaves generated by microwave source 22. An ultrasonic transducer 26 can generate an ultrasonic audio waveform. Controller 24 can include suitable circuitry for pulsing and synchronizing the hypersonic audio waveform and microwave waveform. Battery 28 can power the various components.

The components above are readily available, and their function and design will be readily understood by one of ordinary skill in the art having possession of this disclosure. Some suitable, non-limiting examples of the components include: An RF antenna with gain relative to 4π of 30 dB. The microwave source can produce 10 Watts at 10 GHz. A ceramic ultrasonic transducer can generate between about 120 dB to about 140 dB at 50 kHz (measured at the subject). The microwave frequency utilized can range from 1 GHz to 100 GHz.

While the embodiment illustrated in FIG. 5 can be configured to be relatively highly directional, in one embodiment the emitter arrangement can be configured to be dispersed over a large area. In this embodiment, multiple subjects can be targeted with one or more sources directed across an expansive area. In this manner, many people, for example an opposing force or an unruly mob, can be affected at the same time with the same unit or a number of units.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the examples.

We claim:

1. A method for covertly creating adverse health effects in a human subject, comprising:
   generating at least one electromagnetic wave at a frequency within the range of about 300 MHz (megahertz) and about 300 GHz (gigahertz);
   pulsing the at least one electromagnetic energy wave at a pulse frequency within a target range of human neural oscillations;
   remotely transmitting the at least one pulsed electromagnetic wave to the subject's brain;
   wherein the pulse frequency is continuously varied within the target range of frequencies so as to sweep through the target range of frequencies.

2. The method of claim 1, wherein the target range of human neural oscillations is from about 8 Hz (hertz) to about 12 Hz.

3. The method of claim 1, wherein the target range of human neural oscillations is from about 12.5 Hz to about 30 Hz.

4. The method of claim 3, wherein the target range of human neural oscillations is from about 12.5 Hz to about 16 Hz.

5. The method of claim 3, wherein the target range of human neural oscillations is from about 16.5 Hz to about 20 Hz.

6. The method of claim 3, wherein the target range of human neural oscillations is from about 20.5 Hz to about 28 Hz.

7. The method of claim 1, wherein the pulse frequency corresponds to one of a plurality of discrete frequencies within the target range of frequencies.

8. A method for covertly creating adverse health effects in a human subject, comprising:
- generating at least one ultrasonic audio wave at a frequency greater than about kHz (kilohertz);
- pulsing the at least one ultrasonic audio wave at a pulse frequency within a target range of human neural oscillations;
- remotely transmitting the at least one ultrasonic audio wave to the subject's brain.

9. The method of claim 8, wherein the target range of human neural oscillations is from about 8 Hz (hertz) to about 12 Hz.

10. The method of claim 8, wherein the target range of human neural oscillations is from about 12.5 Hz to about 30 Hz.

11. The method of claim 8, wherein the pulse frequency corresponds to one of a plurality of discrete frequencies within the target range of frequencies.

12. The method of claim 8, wherein the pulse frequency is continuously varied within the target range of frequencies so as to sweep through the target range of frequencies.

13. A method for covertly creating adverse health effects in a human subject, comprising:
- generating at least one electromagnetic wave at a frequency within the range of about 300 MHz (megahertz) and about 300 GHz (gigahertz);
- pulsing the at least one electromagnetic energy wave at a pulse frequency within a target range of human neural oscillations;
- generating at least one ultrasonic audio wave at a frequency greater than about 20 kHz (kilohertz);
- pulsing the at least one ultrasonic audio wave at the pulse frequency;
- remotely transmitting each of the at least one pulsed electromagnetic wave and the at least one ultrasonic audio wave to the subject's brain.

14. The method of claim 8, wherein the target range of human neural oscillations is from about 8 Hz (hertz) to about 30 Hz.

15. The method of claim 8, wherein the at least one ultrasonic audio wave is phased relative to the at least one electromagnetic wave by a delay of Dt of between about 10 ms to about 50 ms seconds.

* * * * *